United States Patent
Fenchel et al.

(10) Patent No.: US 7,899,227 B2
(45) Date of Patent: Mar. 1, 2011

(54) METHOD FOR CONTROLLING THE ACQUISITION AND/OR EVALUATION OPERATION OF IMAGE DATA IN MEDICAL EXAMINATIONS

(75) Inventors: Matthias Fenchel, Tübingen (DE); Andreas Schilling, Gomaringen (DE); Stefan Thesen, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 986 days.

(21) Appl. No.: 11/736,674

(22) Filed: Apr. 18, 2007

(65) Prior Publication Data
US 2007/0242865 A1  Oct. 18, 2007

(30) Foreign Application Priority Data
Apr. 18, 2006  (DE) .................. 10 2006 017 932

(51) Int. Cl.
*G06K 9/00*  (2006.01)

(52) U.S. Cl. ................. 382/128; 382/131; 382/154; 382/285; 382/294; 382/299

(58) Field of Classification Search ............. 382/128, 382/131, 154, 285, 284, 294, 299
See application file for complete search history.

(56) References Cited

U.S. PATENT DOCUMENTS

| | | | |
|---|---|---|---|
| 6,711,432 B1 * | 3/2004 | Krause et al. | 600/427 |
| 7,194,295 B2 * | 3/2007 | Vilsmeier | 600/416 |
| 7,251,522 B2 * | 7/2007 | Essenreiter et al. | 600/424 |
| 2003/0185346 A1 | 10/2003 | Vilsmeier | 378/165 |

* cited by examiner

Primary Examiner—Tom Y Lu
(74) Attorney, Agent, or Firm—Schiff Hardin LLP

(57) ABSTRACT

In a method for controlling the acquisition and/or evaluation operation of image data in medical examinations, using a statistical model of the target volume based on data about real anatomy, spatial information (in particular position, orientation and shape) of the target volume are automatically determined in a previously-acquired planning image data set wholly or partially showing a target volume, and the acquisition and/or evaluation operation is controlled using the spatial information.

23 Claims, 3 Drawing Sheets

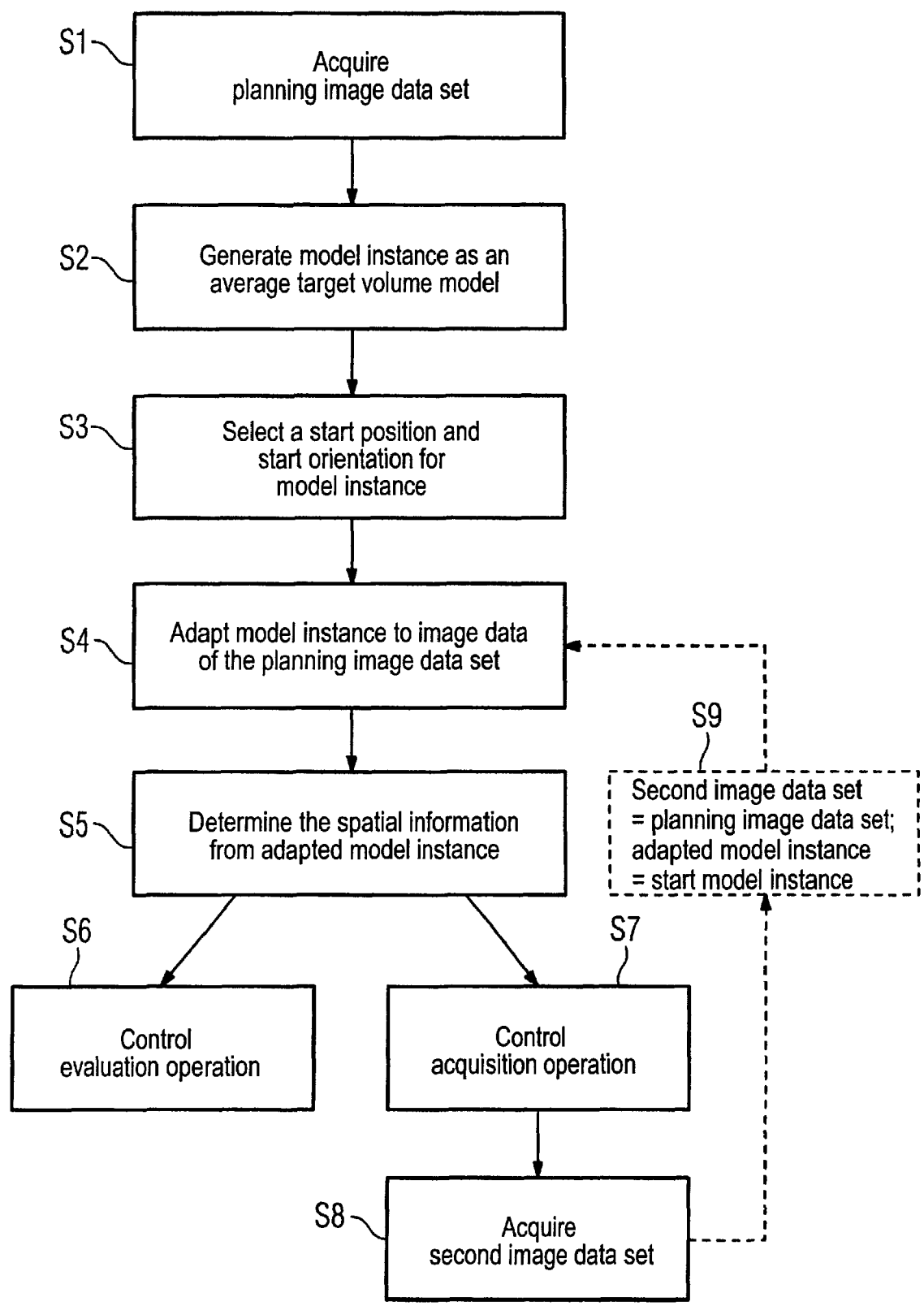

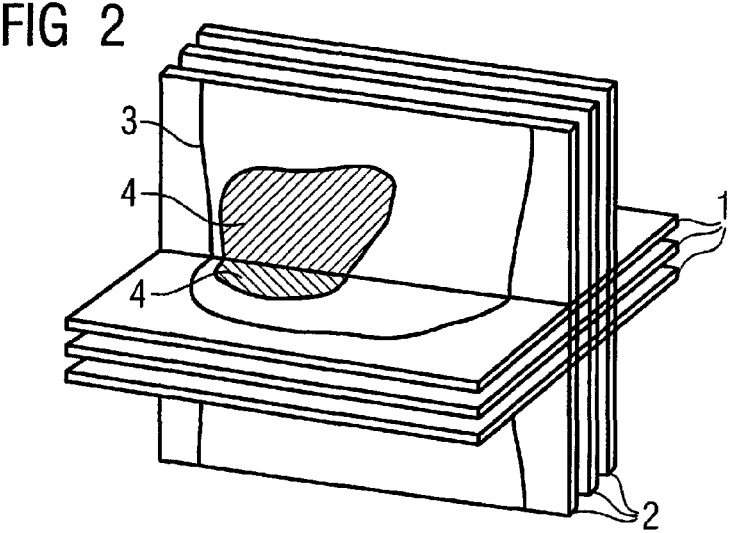
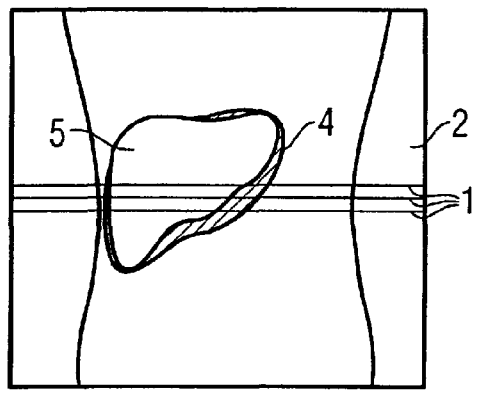
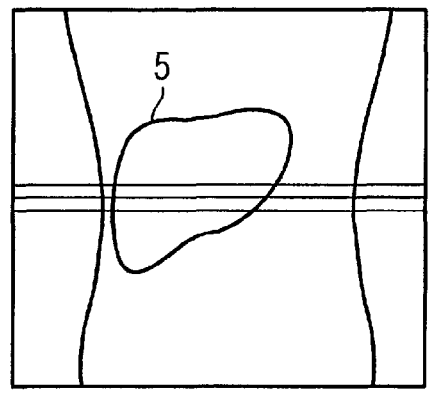
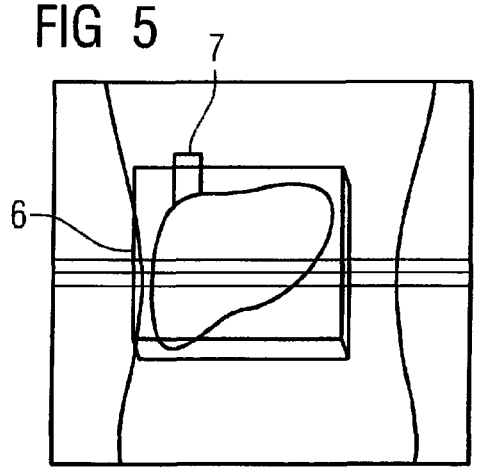

| Organ | Volumes (l) | Lesion Load |
|---|---|---|
| Liver | 1.371 | 0.13 |
| Spleen | 0.173 | 0.01 |
| Kidney | 0.413 | 0.08 |

METHOD FOR CONTROLLING THE ACQUISITION AND/OR EVALUATION OPERATION OF IMAGE DATA IN MEDICAL EXAMINATIONS

BACKGROUND OF THE INVENTION

1. Field of the Invention

The present invention concerns a method for controlling the acquisition and/or evaluation operation of image data in medical examinations.

2. Description of the Prior Art

In routine organ examinations (in particular with a magnetic resonance apparatus) the physician must manually set the acquisition regions for acquisition of a target area surrounding the organ. This usually occurs using scans that are acquired anyway (known as localizers) that (often in low resolution and formed of only a few slices) should serve for location of the target area. The user thereupon views these localizer exposures displayed on a suitable display means and therein places the acquisition areas manually.

If the target volume or organ is arranged in a target area that moves in a cycle, for example due to respiration or heart activity, navigators are frequently also placed. Navigators are markings that mark a specific small region of the target area in which important parameters for the acquisition are then determined. For example, it is known to set a navigator through which a clearly recognizable edge contour of the considered organ proceeds substantially perpendicularly. When the patient breathes, the edge of this organ cyclically shifts with the respiration movement such that the respiration phase is concluded from the current position of this edge and can be used, for example, for triggering or to determine the respiration phase. With rapidly operating systems it is even possible to also implement these observations for the heart phase. One- or three-dimensional navigators are also known in which a point or a whole surface piece is considered. In order to make full use thereof, these navigators must be set exactly; in particular in the above case, the borders of the organ must be perpendicular to the navigator.

Moreover, such markings are also effected in the form of regions of interest in image data sets given the evaluation of these image data sets. For example, organs segmented manually and provided with an identifier so that distinctive features (landmarks) can be associated with them. Such manual markings are frequently also necessary in the region of the start points and borders for segmentations.

Such manual markings or selection processes are, however, generally very error-prone. For example, systems with which localizer exposures are used are particularly error-prone, since the resolution and slice count are usually low and the entire target volume is not covered by them. The exact positioning of the mentioned navigators is likewise critical and error-prone. In addition to the mentioned tendency toward error, the high time expenditure for such a manually implemented procedure is a further disadvantage of the known procedure.

SUMMARY OF THE INVENTION

An object of the present invention is to provide a method with which the susceptibility to error of the control of the acquisition and/or evaluation operation of image data is reduced, and the procedure is accelerated.

This object is achieved in accordance with the invention by a method of the aforementioned type but wherein spatial information (in particular position, orientation and shape) of the target volume are determined in a previously acquired planning image data set wholly or partially showing a target volume, this determination being made using a statistical model of the target volume based on data about real anatomy, and the acquisition and/or evaluation operation is controlled using the spatial information.

According to the invention it is thus proposed to use a statistical model of the target volume for localization that is based on data about real anatomy, so as to obtain spatial information (in particular position, orientation and shape) about the target volume. Such a statistical model can be determined, for example, using image exposure data of a number of persons. If a statistical model (for example of an organ as a target volume) should be generated from thus, the image exposure data of a person are initially taken as a basis. The target volume surface is modeled as a discrete polygonal mesh having nodes, edges and triangles. The coordinates of the points of the model arising from this for the image exposure data are combined into a single vector that is 3n-dimensional when, for example, n points are considered. This procedure is repeated for the image exposure data of each person. Finally, from the vectors determined from this a covariance matrix whose eigensystem describes the statistical correlations can also be determined. The resulting model ultimately comprises an average shape of the target volume and an orthonormal matrix whose columns comprise the eigenvectors of the covariance matrix. In other words, one obtains an average shape of the surface of the target volume and a description as to the extent the shape of this surface can typically deviate, are obtained. Since real data (advantageously such with a certain scattering) are used, every real, existing target volume should be capable of being described by the average shape and a certain deviation therefrom. The statistical model can consequently embody the average shape (thus an average target volume model) and a matrix that contains information about allowed deviations. The acquisition described herein of such a statistical model based on real data is only exemplary; such a model can naturally also be acquired in another manner.

Such a statistical model based on real data primarily offers the advantage that it is extremely realistic, and ultimately (since every target volume, in particular every organ, has a specific shape from which there is only a defined measure of deviation even in different people) the spatial information of the actual target volume is also found since only this is adapted to the predetermined model and most target volumes of different people can also be described by the model. Since a specific basic shape is assumed, not only is a determination of the spatial information of the actual target volume assured but, in contrast to other segmentations, the automatically implemented procedure is additionally accelerated since the basic shape is known and only small details must be adapted. The susceptibility to error is thereby also significantly reduced. The user must consequently specify only the target volume, for example as the liver or another organ, whereupon the spatial information are determined quickly and with high precision by means of the planning image data set and the statistical model without further manual inputs being required. Information as to which target volume should be examined can also be determined from electronic media, for example from a patient record.

Relative to the manual methods that have been conventionally used, the inventive method additionally offers a substantial time savings for the user, who does not have to first laboriously mark regions himself or herself.

Spatial information of the target volume is consequently acquired with the statistical model. In addition, for determination of the spatial information a start position for a generated model instance of model can initially be established under consideration of the type of the target volume, in particular using an ellipsoid model of the torso of a patient, and the model instance can be adapted to the image data in a planning image data set in an optimization process, whereby the spatial information is acquired from the adapted model instance after conclusion of the optimization process.

A start position must consequently be found first. How this can best be established depends on the type of the target volume. For example, if it is an organ arranged in the torso of a patient, its rough position in the torso is relatively well known. For example, for automatic location of the start position the torso can be understood in a simplified manner as an ellipsoid. The position in the ellipsoid at which the corresponding organ is typically located is then assumed as a start position. In practice the first and second moments from the image data set are additionally determined, according to which moments the ellipsoidal torso wherein the start position can then be selected can be determined.

After this a typical optimization process is implemented. This occurs in at least six parameters. The six parameters predetermined anyway are the spatial coordinates of a marked point, for example the focal point of the concrete realization of the model for the current target volume, the model instance and the angle of the orientation of this model instance. The remaining parameters used are internal parameters of the model. In addition to the six spatial and orientation parameters, it has proven to be advantageous to implement the optimization in four to eight (in particular six) further internal model parameters. From calculations it has been shown that six parameters are sufficient in order to describe more than 95% of the variance of the data. The value range of the parameters can thereby be limited in order to acquire only valid and reasonable values. Such a limitation can also be applied to the spatial coordinates or, respectively, the spatial angle. After conclusion of the optimization the model instance is then precisely adapted to the actual existing target volume in practice. The spatial information of the target volume thus can now be determined from the parameters of this adapted model instance, however, more than six parameters (in particular scalings) can also be used.

Depending on the application field, various two-dimensional or three-dimensional data sets or, respectively, data sets from a number of two-dimensional images are considered as a planning image data set. It is possible to use localizer exposures as a planning image data set. Since a statistical model based on real data is used, thus from the outset assumptions about the actual appearance of the target volume are inserted into the method, even low-resolution image data sets with a small coverage of the target area comprising the target volume are sufficient, such that they can be used as a planning image data set. The inventive method herein has a particularly advantageous application field since these localizer exposures are produced anyway before every second image data set acquisition. Conventionally it has been regarded as not possible or only possible with great difficulty to implement a segmentation in these localizer exposures. By the use of the statistical model this is possible in a very error-resistant manner. The invention therewith also advantageously is distinguished from known automatic spatial determination methods (such as "Auto-Align Head" or "Auto-Align Spine") with which special measurement sequences or even entire 3D acquisitions are required.

Naturally it is also possible to use a previous diagnostic image data set as the planning image data set. Such a diagnostic image data set can have already been acquired for various reasons or can be directly evaluated with using the method. For example, an organ in a diagnostic image data set can thus be localized in order to subsequently determine parameters (such as, for example, its volume).

If the spatial information have been determined, the acquisition and/or evaluation operation can now be controlled automatically. A set of control commands that are directed towards the corresponding image acquisition device and/or evaluation device can thus be generated from the spatial information without the assistance of an operating personnel.

As already mentioned, the inventive method can be used for controlling the further acquisition operation of image data, thus for controlling the corresponding image acquisition device. The acquisition of a second image data set (in particular of a magnetic resonance image data set) can be controlled using the spatial information. This is advantageous when the image acquisition device used for acquisition of the planning image data set is used for acquisition of the second image data set. The planning image data set can in turn comprise localizer exposures. The patient appropriately remains essentially unmoved between the acquisition of the second image data set and the acquisition of the planning image data set.

Alternatively, it is also possible to achieve an overview image data set, the panning image data set being registered with the overview image data set, and the second image data set being acquired with the patient unmoved in comparison to the overview image data set, whereby the control of the acquisition ensuing using the registration and the spatial information. Such a scenario can occur, for example, with a diagnostic data set acquired from a temporally prior examination or even another image data set is used as a planning image data set. Naturally it is then also necessary to establish a correlation between the planning image data set and the coordinate system of the image acquisition device or the current support and position of the patient. This occurs using the overview image data set. It can, for example, again concern localizer exposures.

The acquisition of the second image data set can be controlled in various ways. The spatial information thus can be used for determination of image acquisition parameters of slices to be acquired. This is primarily helpful given magnetic resonance acquisitions. The laborious manual marking of slices to be acquired in a display of the planning image data set is also done away with. Alternatively or additionally, the spatial information can be used for positioning of a navigator. As described above, given such navigators it is particularly important to place them optimally exactly at a suitable position. Using known position, orientation and shape of the target volume, it is easily possible by means of suitable algorithms to enable an ideal positioning of the navigator that is far less error-prone.

Furthermore, the spatial information can be used for positioning of the patient. In this case a patient positioning system is activated. For example, an ideal positioning of a patient bed in a magnetic resonance apparatus can be determined such that maximum homogeneity prevails in the target volume.

As a last example it is advantageous to use the spatial information for adaptation of a measurement protocol in magnetic resonance acquisitions. For example, the repetition time can be optimized given what are known as linking acquisitions.

It is often also possible to acquire a larger number of image data sets in the framework of a complete examination or an examination in a plurality of steps. For continuous improvement and optimization of the spatial information it can thereby be reasonable when the second image data set is used as a planning image data set for a further implementation of the method. The establishment of the spatial information is therewith iteratively, steadily improved from acquisition to acquisition, whereby the results of the last adaptation of the statistical model can always be used as start values.

Since, given the adaptation of the model to the corresponding patients, the same adapted model instance ultimately results given differing exposures (thus in differing image data sets), these ultimately differ only due to the positioning of the patient during the acquisition (thus in terms of support and positioning) and possibly due to deformations. Nevertheless, the two mentioned image data sets can be linked by comparison of the plotted points of both of these model instances. The first and second spatial information can be acquired from a first planning image data set acquired in a first examination and a second planning order distribution system serving for planning of a follow-up examination, with both the first spatial information and the second spatial information being used for control. For example, in the first planning image data set a specific point thus can be located at which, for example, an irregularity exists that should be examined more precisely in the framework of a follow-up examination. Since the model instances significantly correspond, the same point of interest can naturally also be located in the instance of the statistical model adapted to the second planning image data set. The items of spatial information acquired from both image data sets are thus advantageously brought into correlation with one another in order to localize the actual area of interest for the follow-up examination in the second planning image data set and to subsequently control the follow-up examination operation. In summary, given different position, orientation and/or shape of the target volume during the acquisition of the first planning image data set and during the acquisition of a further image data set that is to be controlled, the first spatial information and the second spatial information serve for determination of a spatial relationship (in particular a registration) on the basis of which the control ensues. A simple registration is consequently possible using the method.

In another variant of the method, evaluation information about the target volume can be determined under consideration of the spatial information in the framework of a control of the evaluation operation; an evaluation device (that can also be integrated with an image acquisition device) is then accordingly controlled. For example, a start value for a segmentation process can be determined from the spatial information. Where the adaptation of the statistical model alone already shows a quite good segmentation, it can be used as a start point for a finer segmentation algorithm, for more precise and better results.

Alternatively or additionally, the spatial information can be used for to determine physiological parameters or data. Such parameters or data can be, for example, the volume of an organ or, respectively, the number of the lesions occurring therein. The blood circulation of the target volume can also be determined. The spatial information are thereby primarily used to limit the region used to obtain the parameters or data. For example, only the portion from the image data set that also belongs to the target volume is thus considered, and the physiological parameters or data are then determined from this sub-image data set.

The method is also applicable when a number of target volumes are to be seen in a planning image data set. Spatial information of all target volumes can then be determined using one respective statistical model per target volume. For example, in a subsequent step an image acquisition device can be controlled such that, for each of these target volumes, second image data sets that show only this target volume are generated. The method apparatuses proves to be particularly advantageous given the association of conspicuities with specific target volumes or, respectively, organs. The spatial information can then be used for association of determined physiological parameters or data with target volumes. For example, the number of lesions for all organs of the lower abdomen can therewith be displayed. For this purpose, such lesions are initially determined in the entire planning image data set, inclusive of their position. If the position then lies within a target volume localized with the aid of the statistical model, thus within the target volume of a specific organ, it is associated with this organ. This is naturally possible not only for lesions but also for other anomalies (such as, for example, carcinomas) that are then associated with various target volumes.

DESCRIPTION OF THE DRAWINGS

FIG. 1 is a flowchart of an embodiment of the inventive method.

FIG. 2 substantially illustrates localizer images of an area around the liver.

FIG. 3 schematically illustrates localizer exposures with start position and start shape of the model instance.

FIG. 4 substantially illustrates localizer exposures with an adapted model.

FIG. 5 substantially illustrates localizer exposures with an adapted model and marked slices as well as marked navigator.

DESCRIPTION OF THE PREFERRED EMBODIMENTS

Figures 6, 7:
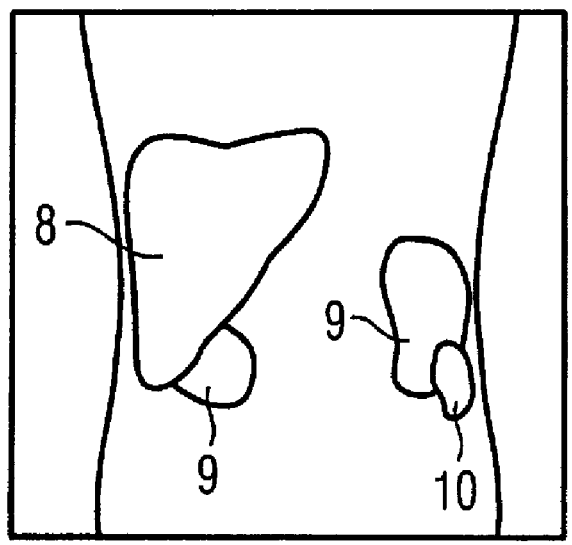
FIG. 6 substantially illustrates a planning image data set with a number of target volumes and model.
FIG. 7 shows an example of the evaluation results of the planning image data set of FIG. 6.

FIG. 1 shows the basic workflow of the inventive method in a flowchart. This will initially be described generally; specific application cases are explained based on FIGS. 2 through 5 and 6 and 7.

The planning image data set is initially acquired in step S1. In the inventive method, any two-dimensional or three-dimensional image data set that shows a specific target volume (for example an organ) can be used as a planning image data set. Next, spatial information about the target volume (in particular position, orientation and shape) should now be determined automatically and optimally without error. In the inventive method a statistical model based on real data serves for this, which statistical model comprises (for example) an average target volume model and a matrix (acquired, for example, via primary component analysis) that comprises information about allowed deviations. The average target volume model is thereby to be understood as an average shape; the matrix specifies to what extent there can be deviation from this determined average shape.

If the statistical model is based on, for example, n points that describe the surface of the target volume, essentially any real shape of the target volume visible in planning image data can thus be described as a 3n-dimensional vector that comprises the points describing the surface. Each of the 3n-dimensional vectors x allowed in this model represents a specific realization of the model that should be called a model instance in the following. Each model instance allowed by the model (consequently every 3n-dimensional vector x) can accordingly be described by the following equation:

$$x = \bar{x} + P \cdot b$$

whereby is a 3n-dimensional vector describing the average target volume model or, respectively, the average shape, P is an orthonormal matrix whose columns comprise the eigenvectors of the covariance matrix and b the feature vector that contains the internal parameters of the model. The feature vector consequently describes the magnitudes of the individual eigenvectors for generation of the model instance x.

The goal is now to adapt a model instance to the real target volume recognizable in the planning image data set. For this purpose, a model instance must initially be generated in step S2. In this regard, for example, the average volume model (thus the average shape) is initially selected in which the vector b has only zeroes. A start position and a start orientation for the model instance with regard to the planning image data set must then selected in step S3. For this one utilizes known information about the anatomical nature of the target volume. For example, the target volume is the liver, it is thus known that this is located in an essentially known orientation at an essentially known position in the right abdominal region. If the torso of the examined patient that is recognizable in the planning image data set is now considered abstracted into an ellipsoid model, a start position and a start orientation can thus be selected. Through the abstracted consideration in which the moments of the first order and the second order in the planning image data set are used to determine the start position and the start orientation, a usable starting point for the adaptation of the model instance to the image data of the planning image data set is achieved in a manner that is advantageous in terms of time.

This adaptation of the model instance to the image data of the planning order distribution system ensues in step S4. This can occur with an optimization method. A correlation metric is initially defined, meaning that a function of the parameters of the statistical model exists that is at a maximum when an ideal correlation (meaning adaptation) exists. Twelve optimization parameters have thereby proven to be sufficient to describe more than 95% of the variance of the data. In addition to the three spatial coordinates and the three orientation angles of the focal point, the inner parameters of the model in the feature vector b of the model server as optimization parameters. However, the six most important parameters of the twelve internal parameters are usually sufficient. The six parameters associated with the largest eigenvalues in the primary component analysis are thereby advantageously selected. Other selection criteria or linked parameters are also conceivable. For example, the correlation of the model surface with the magnitude of the gradients in the planning image data set can serve for calculation of the correlation metric.

This correlation metric is optimized with a standard optimizer according to the cited twelve parameters of the model. Naturally, exactly six internal parameters do not thereby have to be used. The number of the used internal parameters of the model (m) must be selected such that a sufficient variance of the model is ensured, however such that the calculation time remains within acceptable boundaries. During the optimization the value range of the parameters is additionally limited in order to obtain only valid and reasonable values. If, for example, a liver is considered as a target volume, the value range of the spatial coordinates is reasonably limited to ±25 cm from the start position; the value range of the orientation angle is limited to ±15° from the start orientation. The inner parameters are limited in that they may deviate only by double the associated eigenvalue of the result of the primary component analysis.

If the optimization is successfully concluded, the spatial information can be gained from the adapted model instance in step S5. This is possible since the adapted model instance now describes with low error the position, orientation and shape of the actual target volume.

There are essentially two possibilities for use of the acquired spatial information. Both can be used alternatively or also jointly. The evaluation operation can be controlled under consideration of the spatial information. For example, physiological parameters or data are thereby acquired from the planning image data set with the aid of the spatial information. This occurs in step S6. In step S7 the other option is described, namely the control of the acquisition operation of a second image data set under consideration of the spatial information. Namely, if the position, orientation and shape of the target volume are known, the image acquisition device used for acquisition of the second image data set (which can advantageously be the same image acquisition device with which the planning image data set was acquired) can be adjusted (set) such that the target volume can be acquired in the desired manner.

The acquisition of the second image data set then ensues in step S8.

Optionally, it is possible to operate the method iteratively during a longer examination series in which many different image data sets are acquired. The acquired second image data set can serve as a planning image data set for a further implementation of the method; the adapted model instance serves as a new start model instance. Both start position and start orientation are defined as the end values of the optimization of the previous method cycle. This is indicated in step S9. A further adaptation of the model instance subsequently occurs in the new planning image data set (which, for example, shows the target volume in better resolution or better contrast).

The control of the acquisition operation of a liver at a magnetic resonance apparatus should now be described as a first concrete application example of the inventive method. Given acquisitions at magnetic resonance apparatuses it is typical to initially acquire what are known as localizer exposures. These are fast acquisitions of a few slices that do not necessarily cover the entire target area in all dimensions, which slices are often acquired at low resolution. Since many basic assumptions and facts about the anatomy already enter into [sic] due to the use of the statistical model based on the real data, such localizer exposures can be used as a planning image data set.

FIG. 2 is a schematic drawing of such localizer exposures. Three axial slice exposures 1 and three coronal slice exposures 2 of the abdominal region 3 of a patient were acquired in this exemplary embodiment. Parts 4 of the actual target volume (the liver) are respectively visible in these exposures.

A model instance is now generated from a statistical model (based on real data) of the liver that was acquired from the exposures of multiple people and, as described in step S3, a start position and a start orientation are selected for the model instance.

FIG. 3 shows a further schematic drawing of the localizer exposures, wherein a coronal view was selected. Only one of the coronal exposures 2 is therefore visible; the axial exposures 1 are only indicated. The reference characters 5 identify the three-dimensional model instance arranged in the localizer exposures (the planning image data set), which three-dimensional model instance here still has the shape of the average target volume model, such that portions 4 of the liver (thus of the target volume) are still visible.

As described above, in step S4 the model instance is subsequently adapted to the image data of the localizer exposures. The result of this optimization process is visible in FIG.

4, which shows the same view as in FIG. 3 with only a model instance 5 completely adapted in the interim.

If the spatial information is acquired from the adapted model instance in step S5, the acquisition operation of the second image data set (step S7) can now be controlled. A region of interest (ROI) can be generated from the adapted model instance, which region of interest is described by a center and three orthogonal span vectors with axial, sagittal and coronal components. This ROI is designated in FIG. 5 with the reference character 6. Using the spatial information and/or the known ROI 6, a navigator 7 has additionally been marked that, in the acquisition operation, uses the movement of a surface region or, respectively, surface point of the liver for established of (in this case) the respiration phase. If, for example, the heart should be acquired, the EKG phase can also be detectable with the aid of such a navigator.

The acquisition of the second image data set (namely of a high-resolution magnetic resonance image of the liver) can ensue after this. This is advantageously possible without a user intervention. In the framework of the method it is then also possible to use the determined, adapted model instance (as a start model instance) for further adaptation in the second image data set (as a planning image data set) (see step S9). Since position, orientation and shape of the liver are already very well known, a further optimization is implemented quickly that supplies even more precise spatial information that can then be used for further control of the evaluation operation and/or of the acquisition operation of further image data sets.

FIG. 6 shows a schematic drawing of a further planning image data set that has a number of target volumes. These are the liver 8, the kidneys 9 and the spleen 10. A statistical model is now provided for each of these target volumes, thus a statistical model of the liver, a statistical model of the kidneys and a statistical model of the spleen. A model instance is now generated for each of these models and, as described by the steps S3 and S4, are adapted to the image data in the planning image data set. Spatial information about all cited organs can be determined from this. It is also conceivable to additionally model the relative spatial information (bearing) of the organs among one another. Various evaluations are now effected with the aid of the spatial information in the evaluation of the planning image data set. The volume of the individual organs is initially to be determined using the spatial information, in particular the shape of the organs. However, conspicuous tissue is additionally also sought, in particular lesions or tumors. This occurs in the entire planning image data set. Using the spatial information, the detected anomalies (here lesions) can easily be associated with the various organs such that what is known as the "lesion load" can be determined for each organ. This is thereby the ratio of the volume in which lesions are present to the total volume of the corresponding organ.

FIG. 7 shows an example of how the results of the evaluation can be displayed. The organ, its volume and the "lesion load" are respectively shown in the columns of a table 11.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling at least one of acquisition and evaluation of image data in medical examinations, comprising:

providing, to a computer, a statistical model that is statistical representation based on data representing real anatomy that corresponds to anatomy to be examined that is located in a target volume of a subject;

providing, to said computer, a previously-acquired planning image data set to the computer at least partially showing said target volume in said subject;

in said computer, automatically determining spatial information of said target volume in the subject using said statistical model;

in said computer, automatically generating, from said spatial information, at least one control command signal embodying said spatial information in a form configured to operate am apparatus selected from the group consisting of a medical image data acquisition apparatus and a medical image data evaluation apparatus, and supplying said at least some control command signal to said apparatus and with said apparatus and with said at least one control command signal, controlling said apparatus to acquire or evaluate image data in a medical examination according to said special information embodied in said control command signal.

2. A method as claimed in claim 1 comprising determining said spatial information selected from the group consisting of position, orientation and shape of said target volume.

3. A method as claimed in claim 1 comprising generating said statistical model using exposure data obtained from multiple subjects.

4. A method as claimed in claim 1 comprising generating said statistical model as an average model of said target volume formed by a matrix comprising information regarding permissible deviations from said average target volume.

5. A method as claimed in claim 1 comprising determining said spatial information in said computer by identifying a start position from said model dependent on a type of said target volume, adapting said model in an optimization procedure to image data in said planning image data set, and acquiring the spatial information from the adapted model after said optimization procedure.

6. A method as claimed in claim 5 wherein said spatial information comprises six spatial and orientation parameters, and employing an optimization procedure, to adapt said model, using a plurality, in a range of 4 through 8, further model parameters.

7. A method as claimed in claim 1 comprising utilizing a localizer exposure as said planning image data set.

8. A method as claimed in claim 1 comprising using a previously-obtained diagnostic image data set of said subject as said planning image data set.

9. A method as claimed in claim 1 comprising using said spatial information to acquire a further image data set of said subject.

10. A method as claimed in claim 9 comprising generating said planning image data set using a same image acquisition device as is used for obtaining said further image data set.

11. A method as claimed in claim 9 comprising obtaining an overview image data set of the subject and bringing said planning image data set into registration with said overview image data set, and acquiring said further image data set from the subject with the subject unmoved compared to said overview image data set, and controlling acquisition of said further image data set using said registration and said spatial information.

12. A method as claimed in claim 9 comprising using said spatial information to control image acquisition parameters of slices of the subject in said further image data set.

13. A method as claimed in claim 9 comprising using said spatial information to position a navigator for acquiring said further image data set.

14. A method as claimed in claim 9 comprising using said spatial information to control positioning of the subject for acquiring said further image data set.

15. A method as claimed in claim 9 comprising using said spatial information to adapt a measurement protocol for a magnetic resonance apparatus for acquiring said further image data set with said magnetic resonance apparatus.

16. A method as claimed in claim 1 wherein the step of controlling at least one of acquisition and evaluation of an image data set comprises controlling acquisition of an image data set, and wherein the steps of providing said statistical model, providing said previously-acquired planning image data set, determining said spatial information and controlling said acquisition of said image data set comprise a first implementation of the method, and comprising repeating said first implementation of the method, as a second implementation of the method, using said image data set from said first implementation as the previously-acquired planning image data set in said second implementation of the method.

17. A method as claimed in claim 16 wherein said spatial information determined in said first implementation of the method is first spatial information and wherein said spatial information and wherein said spatial information determined in said second implementation of the method is second spatial information, and using both said first spatial information and said second spatial information to control the acquisition of said image data set in said second implementation of the method.

18. A method as claimed in claim 17 wherein said subject is in a different position during said second implementation of the method compared to a position of the subject during said first implementation of the method, and using said first spatial information and said second spatial information to determine a spatial relationship between the respective positions of the subject in said first implementation and said second implementation of the method.

19. A method as claimed in claim 1 wherein the step of controlling at least one of acquisition and evaluation of said image data set comprises controlling evaluation of said image data set, and comprising determining evaluation information about said target volume using said spatial information and controlling said evaluation using said evaluation information.

20. A method as claimed in claim 19 comprising determining a start value for a segmentation process from said spatial information, as said evaluation information.

21. A method as claimed in claim 19 comprising using said spatial information to determine, as said evaluation information, a physiological characteristic of the subject, selected from the group consisting of physiological parameters and physiological data.

22. A method as claimed in claim 1 comprising providing a statistical model to said computer representing a plurality of different target volumes, and providing a planning image data set to said computer that shows all of said plurality of target volumes, and determining respective sets of spatial information for each of said target volumes in said computer.

23. A method as claimed in claim 22 comprising determining spatial information that associate respective physiological characteristics of the subject, selected from the group consisting of physiological parameters and physiological data of the respective target volumes with each other.

* * * * *